(12) United States Patent
Genghi et al.

(10) Patent No.: US 12,141,966 B2
(45) Date of Patent: Nov. 12, 2024

(54) AI-BASED ATLAS MAPPING SLICE LOCALIZER FOR DEEP LEARNING AUTOSEGMENTATION

(71) Applicant: VARIAN MEDICAL SYSTEMS, INC., Palo Alto, CA (US)

(72) Inventors: Angelo Genghi, Wettingen (CH); Anna Siroki-Galambos, Allschwil (CH); Thomas Coradi, Lenzburg (CH); Mário Joao Fartaria, Palo Alto, CA (US); Simon Fluckiger, Lenzburg (CH); Benjamin M. Haas, Roggwil (CH); Fernando Franco, Zurich (CH)

(73) Assignee: Siemens Healthineers International AG, Steinhausen (CH)

(*) Notice: Subject to any disclaimer, the term of this patent is extended or adjusted under 35 U.S.C. 154(b) by 425 days.

(21) Appl. No.: 17/488,208

(22) Filed: Sep. 28, 2021

(65) Prior Publication Data

US 2023/0097224 A1    Mar. 30, 2023

(51) Int. Cl.
*G06T 7/00* (2017.01)
*G06N 3/045* (2023.01)
(Continued)

(52) U.S. Cl.
CPC .......... *G06T 7/0012* (2013.01); *G06N 3/045* (2023.01); *G06T 7/11* (2017.01); *G06T 7/13* (2017.01);
(Continued)

(58) Field of Classification Search
CPC ......... G06T 7/0012; G06T 2207/10081; G06T 2210/41; G06T 2207/10088;
(Continued)

(56) References Cited

U.S. PATENT DOCUMENTS 6,396,939 B1    5/2002    Hu et al.
6,674,883 B1    1/2004    Wei et al.
(Continued)

FOREIGN PATENT DOCUMENTS

WO    WO-2008/014082 A3    1/2008

OTHER PUBLICATIONS

Archip et al.., "A Knowledge-Based Approach to Automatic Detection of the Spinal Cord in CT Images," IEEE Transactions on Medical Imaging, vol. 21, No. 12, pp. 1504-1516, Dec. 2002, 14 pages.
(Continued)

*Primary Examiner* — Ajibola A Akinyemi
(74) *Attorney, Agent, or Firm* — FOLEY & LARDNER LLP

(57) ABSTRACT

Embodiments described herein provide a method for generating training data for AI based atlas mapping slice localization, and a system and method for using the training data to train a deep learning network. Training data development maps each slice of an input medical image to a position in a full body reference atlas along the longitudinal body axis. The method constructs a landmarking table of 2D slices indicating known anatomic landmarks of a reference subject, and interpolated slices. A final step for obtaining training data uses regression analysis techniques to create a vector of longitudinal axis coordinates of all slices from the input image. The training data is used to train a deep learning model to create an AI-based atlas mapping slice localizer model. The trained AI-based atlas mapping slice localizer model can be applied to generate mapping inputs to autosegmentation models to improve efficiency and reliability of contouring.

18 Claims, 7 Drawing Sheets

(51) Int. Cl.
*G06T 7/11* (2017.01)
*G06T 7/13* (2017.01)
*G16H 30/40* (2018.01)

(52) U.S. Cl.
CPC ... *G16H 30/40* (2018.01); *G06T 2207/20081* (2013.01); *G06T 2207/20084* (2013.01)

(58) Field of Classification Search
CPC . G06T 2207/20081; G06T 2207/20084; G06T 7/11; G06T 2207/30004; G06T 2207/30048; G06T 2207/10132; G06T 2207/10116; G06T 2207/30101; G06T 7/0014; G06T 2200/24; G06T 19/20; G06T 2207/10104; G06T 2207/30008
USPC ......................................................... 382/128
See application file for complete search history.

(56) References Cited

U.S. PATENT DOCUMENTS

| | | | |
|---|---|---|---|
| 6,754,376 | B1 | 6/2004 | Turek et al. |
| 7,004,904 | B2 | 2/2006 | Chalana et al. |
| 7,831,079 | B2 | 11/2010 | Kunz et al. |
| 9,489,733 | B2 | 11/2016 | Seifert |
| 2002/0009215 | A1 | 1/2002 | Armato et al. |
| 2005/0094858 | A1 | 5/2005 | Sirohey et al. |
| 2009/0316975 | A1 | 12/2009 | Kunz et al. |
| 2019/0251694 | A1* | 8/2019 | Han .................... G06T 7/11 |
| 2020/0410672 | A1* | 12/2020 | Katscher ............... G06T 7/0012 |
| 2021/0125707 | A1 | 4/2021 | Rusko et al. |
| 2021/0150714 | A1* | 5/2021 | Buerger ................ G16H 30/40 |

OTHER PUBLICATIONS

Betke et al.., "Landmark Detection in the Chest and Registration of Lung Surfaces with an Application to Nodule Registration," Medical Imaging Analysis, vol. 7, No. 3, pp. 265-281, Sep. 2003, 17 pages.
Brie Goo, Katrina May, Haobo Zhang, James Olivas; "Machine Learning Solution to Organ-At-Risk Segmentation for Radiation Treatment Planning;" Santa Clara University, Interdisciplinary Design Senior Theses; Jun. 13, 2019; 41 pages.
Carlos E Cardenas, Jinzhong Yang, Brian M Anderson, Laurence E Court, Kristy B Brock; "Advances in Auto-Segmentation;" Semin Radiat Oncol. Jul. 2019:185-197; Jul. 2019, 13 pages.
Chenjie Ge, Irene Yu-Hua Gu, Asgeir Store Jakola, Jie Yang; "Deep semi-supervised learning for brain tumor classification"; BMC Medical Imaging vol. 20; Jul. 29, 2020; 11 pages.
F. Vaassen, C. Hazelaar, A. Vaniqui, M. Gooding, B. van der Heyden, R. Canters, W. V. van Elmpt; "Evaluation of measures for assessing time-saving of automatic organ-at-risk segmentation in radiotherapy;" Physics and Imaging in Radiation Oncology, vol. 13, pp. 1-6; Jan. 2020; 6 pages.
Gregory Sharp, Karl D Fritscher, Vladimir Pekar, Marta Peroni, Nadya Shusharina, Harini Veeraraghavan, Jinzhong Yang; "Vision 20-20_Perspectives on automated image segmentation for radiotherapy;" published online Med Phys. May 2014; 41(5): 050902; Apr. 24, 2014; 13 pages.
Pommert et al., "Symbolic Modeling of Human Anatomy for Visualization and Simulation," Visualization in Biomedical Imaging, Proc. SPIE, 2359, pp. 412-423, 1994, 12 pages.
Qatarneh et al., "Evaluation of a Segmentation Procedure to Delineate Organs for Use in Construction of a Radiation Therapy Planning Atlas," International Journal of Medical Informatics, vol. 69, pp. 39-55, Sep. 2003, 17 pages.
Rohr et al., "Landmark-Based Elastic Matching of Tomographic Images," IEEE Transactions on Medical Imaging, vol. 20, No. 6, pp. 526-534, Jun. 2001, 9 pages.
Invitation to Pay Additional Fees on PCT app. PCT/US2022/043202 dated Feb. 15, 2023 (13 pages).
International Search Report and Written Opinion on PCT App. PCT/US2022/043202 dated Apr. 5, 2023 (18 pages).
International Preliminary Report on Patentability for PCT App. PCT/US2022/043202 dated Apr. 2, 2024 (11 pages).

* cited by examiner

AI-BASED ATLAS MAPPING SLICE LOCALIZER FOR DEEP LEARNING AUTOSEGMENTATION

TECHNICAL FIELD

This application relates generally to artificial intelligence-based atlas-mapping for deep learning autosegmentation.

BACKGROUND

Radiotherapy (radiation-based therapy) is used as a cancer treatment to emit high doses of radiation that can kill cancer cells and shrink a tumor. The goal is to deliver enough radiation to a target region of the patient's anatomy to kill the cancerous cells during the radiotherapy treatment. However, other organs or anatomical regions that are close to, or surrounding, the target region can be in the way of radiation beams and can receive enough radiation to damage or harm such healthy organs or anatomical regions. These organs or anatomical regions are referred to as organs at risk ("OARs"). Typically a physician or a radiation oncologist identifies both the target region and the OARs prior to radiotherapy using various imaging modalities. Furthermore, simulation images of the patient's anatomy may be obtained.

For safe and effective radiotherapy treatment, it is crucial to accurately segment target regions and OARs. Due to rapid advances in radiation therapy such as image guidance and treatment adaptation, a fast and accurate segmentation of medical images is a very important part of the treatment. Segmentation generally involves separating irrelevant objects or extracting anatomic surfaces, structures, or regions of interest from images for purposes of anatomic identification, diagnosis, evaluation, and volumetric measurement. Image registration is a process of finding correspondence of points in two different images for facilitating comparisons and medical diagnosis.

Automated segmentation methods, including techniques that incorporate machine learning, seek to reduce delineation workload and unify the organ boundary definition. In deploying automated segmentation to clinical applications, however, segmentation and registration techniques generally require prior anatomic or geometric knowledge about the image content in order to work reliably. Machine learning systems, such as deep neural networks, are trained for auto-segmentation of anatomical organs with real images from clinical routine, such as computerized tomography ("CT") images. These images normally do not cover entire patient body, rather, normally they cover a section of the "cranio-caudal range." Therefore, training data normally includes image volume around a structure of interest, not full body images.

In view of these limitations, automated segmentation deploying machine learning to clinical applications the network may not learn that an organ located in a particular anatomical region is not found in other regions of the body (e.g., brain located in the head). This may result in a false positive. For example, in an image volume of an abdominal region, the network may classify liver tissue as brain. Additionally, when attempting to identify an organ in a CT scan in which the organ is much smaller than the volume of the scan, automated segmentation can require an unnecessarily large period of time in image analysis seeking to classify the entire image volume.

SUMMARY

For the aforementioned reasons, there is a need for systems and methods for automated segmentation that provide knowledge of anatomical regions included in an input CT or other medical image. Discussed herein are autosegmentation techniques for clinical applications with improved segmentation and registration based upon anatomic or geometric knowledge about CTs or other medical images. Disclosed systems and methods for automated segmentation deploying machine learning techniques to clinical applications overcome limitations of conventional training data. Disclosed systems and methods reduce likelihood of false positives based on anatomical structures not found in a region of the body encompassed by a medical image. Embodiments described herein may increase efficiency of image analysis, for example, when seeking to identify an organ that is much smaller than the volume of a CT scan or other medical image.

In an embodiment, a processor-based method executes a machine learning model that receives an input of a first image of an anatomical region of a patient. In an embodiment, the machine learning model receives the first image of the anatomical region of the patient at inference time, e.g., for developing a treatment plan of the patient. The machine learning model may output a mapping of a slice from the first image to a reference image. The first image of the anatomical region of the patient may depict a first organ having an outline to predict boundary information of the anatomical region within the reference image. The processor transmits the boundary information of the anatomical region of the first image to a computer model. The computer model executes a contouring protocol to identify the outline of the first organ within the anatomical region.

In an embodiment, the processor selects the computer model based on the boundary information of the anatomical region. The computer model may be a second machine learning model configured to ingest the first image and identify the contour within the anatomical region. The computer model may be an autosegmentation model that uses the boundary information to run more efficiently in clinical applications using knowledge of anatomical regions of an input medical image. Autosegmentation systems can use the boundary information and mapping to known positions from the reference image to select suitable computer model(s) from a library of computer models for contouring a patient image.

The boundary information may include a first limit and a second limit. In an embodiment, the boundary information includes a vector of longitudinal axis coordinates in a reference space of the first image. In an embodiment, these coordinates may be mapped to known positions, such as anatomical regions, from the reference image.

In an embodiment, the machine learning model is trained based on a set of second images of a set of second anatomical regions depicting a set of second organs having a set of second outlines. In an embodiment, the set of second images include training data derived from medical images of prior patients. At least one second image within the set of second images may be labeled based on a reference point within the at least one second image to a corresponding anatomical region within the reference image.

Systems and methods for AI-based atlas mapping slice localization incorporate a process for generating training data and a process using the training data to train a deep learning network. In process for generating training data, disclosed systems and methods employ AI-based atlas mapping slice localization to map each slice of an input medical image to a position in a full body reference medical image by mapping to longitudinal axis coordinates in a reference space of the reference medical image. The present disclosure refers to longitudinal axis coordinates or longitudinal body axis coordinates in a reference space of the reference medical image or in a reference space of an input image. As an alternative to longitudinal axis coordinates, the present disclosure refers to z-axis coordinates in a reference space of the reference medical image or reference space of an input image. As used in the present disclosure, a slice may represent an axial 2D cross-section along a z-axis of a three-dimensional image such as an input CT or reference CT.

In an embodiment, a method for obtaining training data uses 2D anatomical landmarks. The method constructs a landmarking table relating a set of images representative of a region of interest in a subject to a reference system with reference positions indicating known anatomic landmarks of a reference subject. A final step for obtaining training data maps all slices to the reference atlas image using regression analysis techniques. In various embodiments, the regression analysis techniques may include, e.g., linear regression and piecewise linear regression. This final step creates a vector of longitudinal axis coordinates of all slices from the image to be analyzed.

In an embodiment, a method for training a deep learning model applies labeled data obtained via detection of 2D anatomical landmarks in combination with regression analysis to train an AI based atlas mapping slice localizer model. Upon inputting the labeled data, the deep learning model learns visual attributes of a certain anatomical region and numerical values for the anatomical region that correspond to localized slices within an atlas or reference CT scan. The trained AI-based atlas mapping slice localizer model can be applied to a new input image for mapping slice localization. The trained model outputs a vector of z-axis coordinates in the reference space of the input image. These coordinates may be mapped to known positions (e.g., anatomical regions) from the reference image.

In an embodiment, a method comprises executing, by a processor, a machine learning model that receives an input of a first image of an anatomical region of a patient depicting a first organ having an outline to predict boundary information of the anatomical region within a reference image; and transmitting, by the processor, the boundary information of the anatomical region of the first image to a computer model, whereby the computer model executes a contouring protocol to identify the outline of the first organ within the anatomical region.

The method may further include selecting, by the processor, the computer model based on the boundary information of the anatomical region.

The computer model may be a second machine learning model configured to ingest the first image and identify the contour within the anatomical region.

The machine learning model may output a mapping of a slice from the first image to the reference image.

The machine learning model may be trained based on a set of second images of a set of second anatomical regions depicting a set of second organs having a set of second outlines.

At least one second image within the set of second images may be labeled based on a reference point within the at least one second image to a corresponding anatomical region within the reference image.

The boundary information may comprise a first limit and a second limit.

In another embodiment, a method comprises: upon receiving a set of medical images, determine, by a processor, a plurality of anatomic landmarks from the medical images and determine corresponding landmarks defined on an atlas image; calculate, by the processor, longitudinal axis coordinates for each of the plurality of anatomic landmarks in a first image space of the respective medical image and for each of the corresponding landmarks in a second image space of the atlas image; execute, by the processor, a regression analysis between the anatomic landmarks and the corresponding landmarks; and for each of the medical images, generate, by the processor, a vector of longitudinal axis coordinates mapping the respective medical image to the atlas image.

Each of the anatomic landmarks may be a 2D slice from a respective medical image that matches the corresponding landmark defined on the atlas image.

The atlas image may be a full body atlas, wherein the longitudinal axis coordinates in the second image space of the atlas image are coordinates within a total cranial-caudal range along a longitudinal body axis of the full body atlas.

The regression analysis between the anatomic landmarks and the corresponding landmarks may be a piecewise linear regression.

The regression analysis may employ piecewise linear regression to apply the regression analysis to a plurality of regression segments corresponding to 2D slices from the set of medical images.

The vector of longitudinal axis coordinates for each of the medical images may encompass all 2D slices from the respective medical image.

The vector of longitudinal axis coordinates for each of the medical images may be mapped to the altas image via estimated regression coefficients.

The method may further include training, by the processor, a deep learning model to determine a vector of longitudinal axis coordinates in an image space of an image analyzed by the model, wherein training inputs to the deep learning model comprise the set of medical images and the vector of longitudinal axis coordinates for each of the medical images.

In a further embodiment, a system comprises a server comprising a processor and a non-transitory computer-readable medium containing instructions that when executed by the processor causes the processor to perform operations comprising: execute a machine learning model that receives an input of a first image of an anatomical region of a patient depicting a first organ having an outline to predict boundary information of the anatomical region within a reference image; and transmit the boundary information of the anatomical region of the first image to a computer model, whereby the computer model executes a contouring protocol to identify the outline of the first organ within the anatomical region.

The processor may further be configured to perform operations comprising: select the computer model based on the boundary information of the anatomical region.

The machine learning model may be trained based on a set of second images of a set of second anatomical regions depicting a set of second organs having a set of second outlines.

At least one second image within the set of second images may be labeled based on a reference point within the at least one second image to a corresponding anatomical region within the reference image.

The boundary information may comprise a first limit and a second limit.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

DETAILED DESCRIPTION

Figure 1:
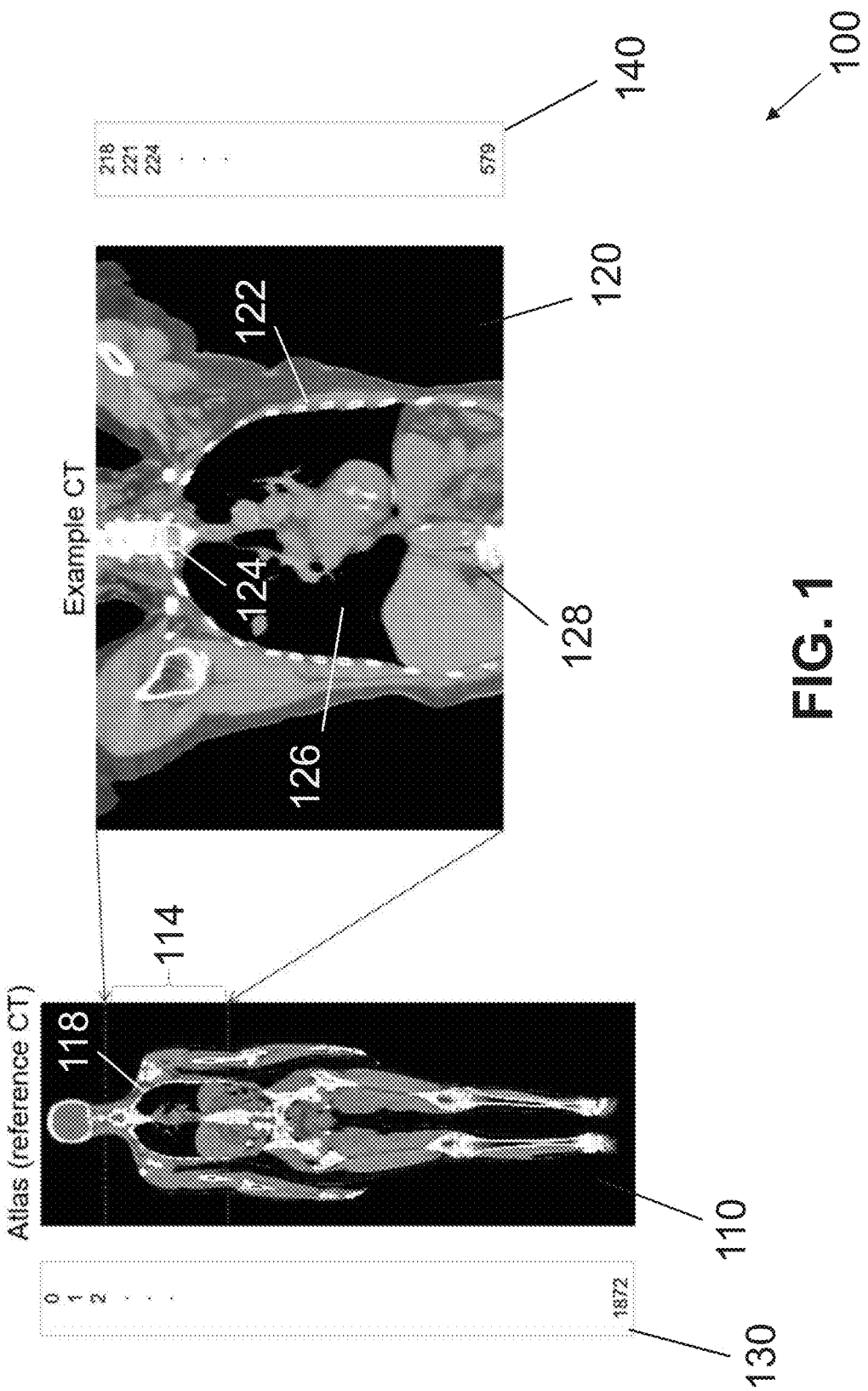
FIG. 1 is a conceptual diagram illustrating mapping of an input medical image against a reference CT image, according to an embodiment.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

When medical imaging is necessary to observe an internal organ or a set of internal organs, there are several systems that may be utilized such as X-ray, CT, cone beam CT images (CBCT), four-dimensional CT images (e.g., CT images over time), magnetic resonance imaging (MRI) images, positron emission tomography (PET) images, ultrasound images, and or a combination thereof. When CT or MRI imagery, for example, is used, a series of two-dimensional images are taken from a three-dimensional volume. Here, each two-dimensional image is an image of a cross-section of the three-dimensional volume. The resulting collection of two-dimensional cross-sectional images can be combined to create a three-dimensional image or reconstruction of the patient's anatomy. This resulting three-dimensional image or three-dimensional reconstruction will contain the desired internal organ. This portion of the three-dimensional image or reconstruction that contains the structure of interest may be referred to as a volume of interest.

Radiation therapy treatment plans are used during medical procedures that selectively expose precise areas of the body, such as cancerous tumors, to specific doses of radiation to destroy the undesirable tissues. An initial treatment plan may be prepared that defines the area in the human body to be treated, such as cancerous tissue, abnormal cells, lesions, and organs, called the clinical target volume (CTV). Another volume known as a planning target volume (PTV) allows for uncertainties in planning or treatment delivery to ensure that the radiotherapy dose is actually delivered to the CTV. Radiotherapy planning generally considers critical normal tissue structures near the CTV, known as organs at risk. The goal is to deliver enough radiation to the PTV to kill the cancerous cells during the radiotherapy treatment. OARs that are close to, or surrounding, the PTV can be in the way of radiation beams and can receive enough radiation to damage or harm such organs or anatomical regions. A physician or a radiation oncologist may identify both the PTV and the OARs prior to radiotherapy using a suitable imaging modality. Furthermore, simulation images of the patient's anatomy may be obtained.

For safe and effective radiotherapy treatment, it may be crucial to accurately segment organs of interest. Segmentation generally involves separating irrelevant objects or extracting anatomic surfaces, structures, or regions of interest from images for purposes of anatomic identification, diagnosis, evaluation, and volumetric measurement. Image registration may be a process of finding correspondence of points in two different images for facilitating comparisons and medical diagnosis.

Automated segmentation methods may employ machine learning techniques to reduce delineation workload. Machine learning systems for auto-segmentation, such as deep neural networks, typically are trained for auto-segmentation of anatomical organs with real CT tomography images from clinical routine. These images normally do not cover the patient's entire body, rather, they normally cover a section of the cranio-caudal range. Therefore, training may use image volume around a structure of interest, not full body images. Full body CT scans are not available in sufficient volume to train detection networks. However, segmentation and registration techniques generally require prior anatomic or geometric knowledge about the image content in order to work most reliably. Disclosed systems and methods address limitations in segmentation and registration of medical images in applying machine learning techniques to automatic segmentation for clinical applications.

Disclosed systems and methods for AI-based atlas mapping slice localization incorporate two main processes: a process for generating training data, and a process for using the training data to train a deep learning network.

In the process for generating training data, disclosed systems and methods employ AI-based atlas mapping slice localization to map each slice of an input medical image to a position in a full body reference medical image by mapping to longitudinal axis coordinates in a reference space of the reference medical image. The present disclosure variously refers to the reference medical image as an atlas, reference CT, or atlas CT.

Disclosed systems and methods obtain training data using 2D anatomical landmarks via the detection method disclosed in US Patent Publication No. 20090316975, Anatomic Orientation in Medical Images, which is incorporated by reference in its entirety. A method may include constructing a navigation table, also referred to herein as a landmarking table, relating a set of images representative of a region of interest in a subject to a reference system with reference positions indicating known anatomic landmarks of a reference subject. For example, the method may including identifying a landmark within an image, such as a bone, and determining the anatomical region associated with the landmark. The method may provide reference positions for two or more images identified with two or more anatomic landmarks indicative of the region of interest, with reference positions of known anatomic landmarks corresponding to the identified anatomic landmarks. The systems and methods may apply interpolation to slices between 2D slices containing the landmarks.

A final step for obtaining training data maps all slices to the reference atlas image. Disclosed systems and methods employ the 2D anatomical landmarks method in combination with regression analysis techniques to generate training data. This training data is subsequently used to train an AI model. In various embodiments, the regression analysis techniques may include, e.g., linear regression and piecewise linear regression. Piecewise linear regression employs the principle of modeling the regression function in "pieces" for data that follows different linear trends over different regions of the data. The independent variable is partitioned into intervals, and a separate line segment is fit to each interval. Piecewise linear regression may be useful when the independent variables, clustered into different groups, exhibit different relationships between the variables in these regions.

In an embodiment of a process for using the training data to train a deep learning network, a 3D deep neural network maps each slice of an input CT scan to a position along the longitudinal body axis in a reference CT. The position of each organ and each anatomical area is known in the reference CT. This method provides an approximate position of each organ and anatomical area in the input CT. As used in the present disclosure, a slice may represent an axial 2D cross-section along a z-axis of a three-dimensional image such as an input CT or reference CT.

Disclosed systems and methods for AI-based atlas mapping slice localization may offer various advantages over prior methods in deploying a process for generating training data in conjunction with using the training data to train a deep learning network. Clinical applications may benefit from deep learning based auto-segmentation that can achieve improved efficiency of image segmentation and improved consistency and objectivity for diagnosis. Deep learning based auto-segmentation without a localizer may be slow or may produce false positives. Deep learning based auto-segmentation with an organ localizer only (very low resolution organ model) may need to be trained on the full body for each organ, which may require considerable training data and time. Atlas mapping slice localizer methods disclosed herein may be more robust in the presence of image artifacts and also work on CBCT images. A 2D slice based approach may classify single slices instead of volume and outputs a label (anatomical region label) per slice. The approach of the present disclosure may provides additional spatial and orientation information (mapping to reference scale).

Present systems and methods can be applied to other medical imaging modalities besides CT (CBCTS, MRI, PET, etc.).

Similar AI-based atlas location methods may extend the 3D deep neural network to applications beyond mapping. One such application is quality control confirmation (by double-checking location) of organs segmented manually or by unknown auto-segmentation. Another application is automatic classification of CT scans by body region in big data collections. Classification can be used for statistical analysis or data retrieval/filtering. A further application is automatic verification of image content for quality and safety assurance (for example detection of patient pose, sex, size, region scanned).

The conceptual diagram 100 of FIG. 1 illustrates mapping of an input medical image against a reference CT image. An example input CT 120 is shown on the right and a reference CT 110 of an atlas 118 is shown on the left. The input CT scan images a volume, and the example CT 120 is a coronal 2D section from this volume. An imaged body region 122 encompassed by input CT 2D section 120 includes part of the neck 124, the full thorax 126, and part of the abdomen 128. Reference CT 110 shows a coronal 2D section of the reference CT image or atlas 118. The reference system can be a scale along the Z-axis of the human anatomy indicating reference positions for known anatomic landmarks in the reference human anatomy A scale 130 of reference coordinates encompasses the total cranial-caudal range of 0-1872 along the longitudinal body axis in the full body atlas 118. In an embodiment, for every point in the input CT the algorithm for atlas mapping identifies where to find that point in the atlas CT. The algorithm for atlas mapping slice localization outputs reference coordinates 114 from the atlas CT encompassing the input CT, e.g., the range 140 from 218 to 579. The algorithm knows the position of each organ and each anatomical area in the atlas 118, hence knows that the reference CT slice 218 in the atlas corresponds to the neck and that reference CT slice 579 in the atlas corresponds to beginning of the abdomen. After mapping all slices of the 3D input CT to the reference CT, the algorithm provides information on organs and anatomical regions included in the 3D input CT.

Figure 2:
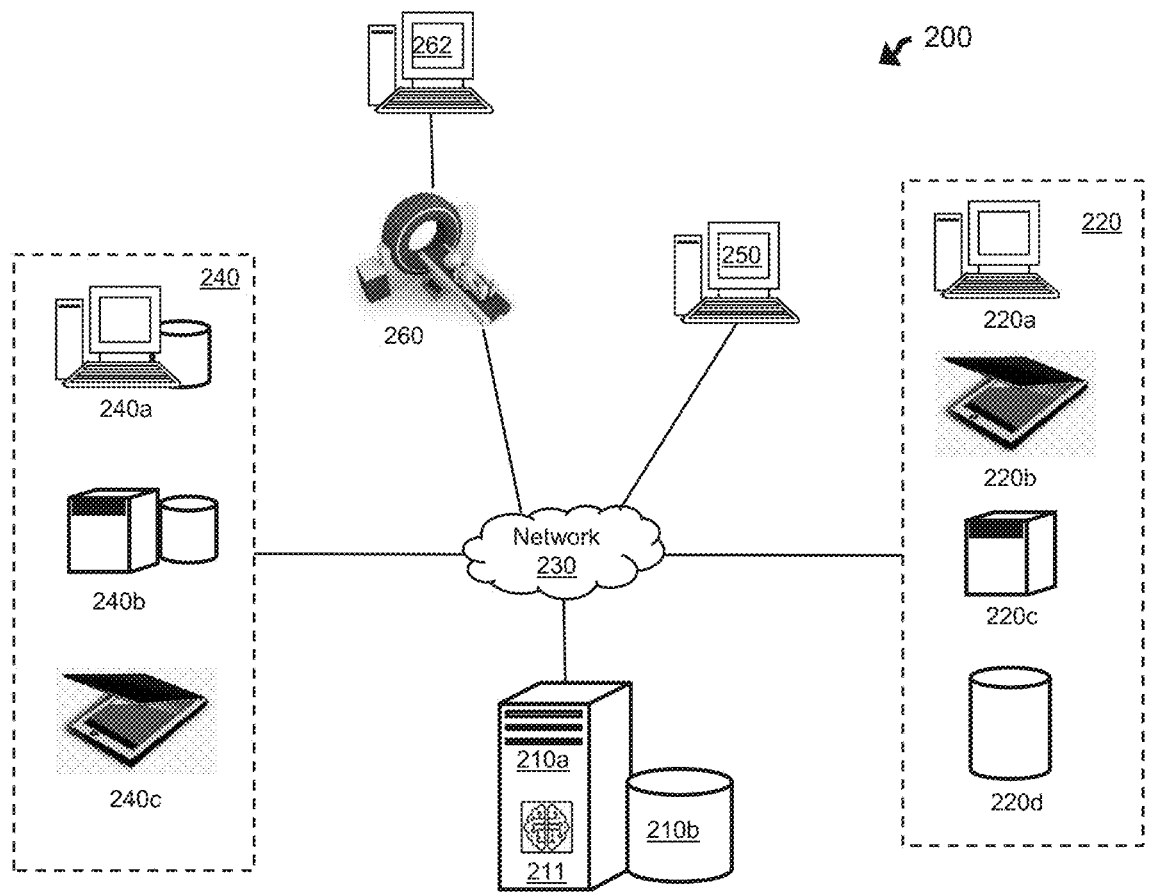
FIG. 2 illustrates components of a system for AI-based atlas mapping slice localization to obtain training data for a deep learning model, and for applying a trained atlas mapping slice localization model in autosegmentation, according to an embodiment.

FIG. 2 illustrates components of a system 200 for applying a trained AI-based atlas mapping slice localizer model at inference-time, e.g., in improved autosegmentation models. In addition, system 200 may apply machine learning techniques in training an AI-based atlas mapping slice localizer. The system 200 may include an analytics server 210a, system database 210b, machine learning models 211, electronic data sources 220a-d (collectively electronic data sources 220), end-user devices 240a-c (collectively end-user devices 240), an administrator computing device 250, and a medical device 260 having a medical device computer 262. Various components depicted in FIG. 2 may belong to a radiotherapy clinic at which patients may receive radiotherapy treatment, in some cases via one or more radiotherapy machines located within the clinic (e.g., medical device 260). The above-mentioned components may be connected to each other through a network 230. Examples of the network 230 may include, but are not limited to, private or public LAN, WLAN, MAN, WAN, and the Internet. The network 230 may include wired and/or wireless communications according to one or more standards and/or via one or more transport mediums.

The system 200 is not confined to the components described herein and may include additional or other components, not shown for brevity, which are to be considered within the scope of the embodiments described herein.

The communication over the network 230 may be performed in accordance with various communication protocols such as Transmission Control Protocol and Internet Protocol (TCP/IP), User Datagram Protocol (UDP), and IEEE communication protocols. In one example, the network 230 may include wireless communications according to Bluetooth specification sets or another standard or proprietary wireless communication protocol. In another example, the network 230 may also include communications over a cellular network, including, e.g., a GSM (Global System for Mobile Communications), CDMA (Code Division Multiple Access), or EDGE (Enhanced Data for Global Evolution) network.

The analytics server 210a may generate and display an electronic platform configured to use various computer models 211 (including artificial intelligence and/or machine learning models) for AI-based atlas mapping slice localization to obtain training data, and for training deep learning models using this data. More specifically, at an inference phase for a patient treatment plan, the electronic platform may display one or more medical images such as images of patient OARs or other internal organs, and images of autosegmentation contours of such organs. The electronic platform may include a graphical user interface (GUI) displayed on each electronic data source 220, the end-user devices 240, and/or the administrator computing device 250. An example of the electronic platform generated and hosted by the analytics server 210a may be a web-based application or a website configured to be displayed on different electronic devices, such as mobile devices, tablets, personal computers, and the like.

Additionally, the electronic platform may display two-dimensional and/or three-dimensional plots output by the artificial intelligence models 211 based upon atlas mapping slice localization, and based upon autosegmentation contours of the prior patient's medical images and the current patient's medical images.

In a non-limiting example, a physician or radiation oncologist operating the medical professional device 220b, 240c may access the platform, review the results of atlas mapping slice localization, and review autosegmentation contours. The physician or radiation oncologist may visually inspect two-dimensional and/or three-dimensional plots based upon atlas mapping slice localization and based upon autosegmentation contours of prior patient and current patient medical images. The medical professional devices (e.g., the medical professional device 240c) may be used as both a device to display results predicted by the analytics server 210a and in some cases as an electronic data source (e.g., electronic data source 220b) to train the machine learning model 211.

The analytics server 210a may host a website accessible to users operating any of the electronic devices described herein (e.g., end users, medical professionals), where the content presented via the various webpages may be controlled based upon each particular user's role or viewing permissions. The analytics server 210a may be any computing device comprising a processor and non-transitory machine-readable storage capable of executing the various tasks and processes described herein. The analytics server 210a may employ various processors such as central processing units (CPU) and graphics processing unit (GPU), among others. Non-limiting examples of such computing devices may include workstation computers, laptop computers, server computers, and the like. While the system 200 includes a single analytics server 110a, the analytics server 210a may include any number of computing devices operating in a distributed computing environment, such as a cloud environment.

The analytics server 210a may execute software applications configured to display the electronic platform (e.g., host a website), which may generate and serve various webpages to each electronic data source 220 and/or end-user devices 240. Different users may use the website to view and/or interact with displayed content.

The analytics server 210a may be configured to require user authentication based upon a set of user authorization credentials (e.g., username, password, biometrics, cryptographic certificate, and the like). The analytics server 210a may access the system database 210b configured to store user credentials, which the analytics server 210a may be configured to reference in order to determine whether a set of entered credentials (purportedly authenticating the user) match an appropriate set of credentials that identify and authenticate the user.

The analytics server 210a may generate and host webpages based upon a particular user's role within the system 200. In such implementations, the user's role may be defined by data fields and input fields in user records stored in the system database 210b. The analytics server 210a may authenticate the user and may identify the user's role by executing an access directory protocol (e.g., LDAP). The analytics server 210a may generate webpage content that is customized according to the user's role defined by the user record in the system database 210b.

The analytics server 210a may receive medical images from a user or retrieve such data from a data repository, analyze the data, and display the results on the electronic platform. For instance, in a non-limiting example, the analytics server 210a may query and retrieve medical images from the database 220d and combine the medical images with segment data received from a physician operating the medical professional device 220b. Additionally, or alternatively, the analytics server 210a may segment the medical image automatically or perform other pre-processing steps on the medical image captured from the medical device 260.

The analytics server 210a may execute various machine learning models 211 (e.g., stored within the system database 210b) to analyze the retrieved data. The analytics server 210a may then display the results via the electronic platform on the administrator computing device 250 and/or the end-user devices 240.

The electronic data sources 220 may represent various electronic data sources that contain, retrieve, and/or input data associated with a patient's treatment plan including patient data and treatment data. For instance, the analytics server 210a may use the clinic computer 220a, medical professional device 220b, server 220c (associated with a physician and/or clinic), and database 220d (associated with the physician and/or the clinic) to retrieve/receive data associated with the patient's treatment plan.

End-user devices 240 may be any computing device comprising a processor and a non-transitory machine-readable storage medium capable of performing the various tasks and processes described herein. Non-limiting examples of an end-user device 240 may be a workstation computer, laptop computer, tablet computer, and server computer. In operation, various users may use end-user devices 240 to access the GUI operationally managed by the analytics server 210a. Specifically, the end-user devices 240 may include clinic computer 240a, clinic server 240b, and a medical processional device 240c. Even though referred to herein as "end user" devices, these devices may not always be operated by end users. For instance, the clinic server 240b may not be directly used by an end user. However, the results stored on the clinic server 240b may be used to populate various GUIs accessed by an end user via the medical professional device 240c.

The administrator computing device 250 may represent a computing device operated by a system administrator. The administrator computing device 250 may be configured to display radiation therapy treatment attributes generated by the analytics server 210a (e.g., various analytic metrics determined during training of one or more machine learning models and/or systems); monitor various models 211 utilized by the analytics server 210a, electronic data sources 220, and/or end-user devices 240; review feedback; and/or facilitate training or retraining (calibration) of the machine learning models 211 that are maintained by the analytics server 210a.

The medical device 260 may be a radiotherapy machine configured to implement a patient's radiotherapy treatment. The medical device 260 may also include an imaging device capable of emitting radiation such that the medical device 260 may perform imaging according to various methods to accurately image the internal structure of a patient. For instance, the medical device 260 may include a rotating system (e.g., a static or rotating multi-view system). A non-limiting example of a multi-view system may include a stereo system (e.g., two systems arranged orthogonally). The medical device 260 may also be in communication with a medical device computer 262 that is configured to display various GUIs discussed herein. For instance, the analytics server 210a may display the results predicted by the machine learning model 211 on the medical device computer 262.

In operation, a physician or other medical professional may access an application executing on the medical professional device 220b and input patient data and the patient's treatment data (e.g., patient information, patient diagnosis, radiation therapy radiation requirements and thresholds). The analytics server 210a then uses a patient identifier to query patient data (e.g., patient anatomy and/or medical images) from the electronic data sources 220. The analytics server may then identify a clinic associated with the patient (e.g., the clinic performing the treatment) and retrieve one or more files associated with treatment templates and clinic rules. The analytics server 210a may utilize the systems and methods described herein to generate AI-based atlas mapping slice localization data based on input patient images.

A medical professional at a radiotherapy clinic may access an end-user device 240 located at the clinic or access an account associated with the clinic. The medical professional may provide an input at a user interface that causes the end user device 240 to transmit a request to access a machine learning model 211 that is associated with the clinic and/or the radiotherapy machines located within the clinic. The request may include an identifier associated with the machine learning model 211, the clinic, a treatment plan generated by the one or more medical professionals, and/or the set of radiotherapy machines that the analytics server 210a may use as a key in a look-up table to identify the machine learning model 211. The analytics server 210a may receive the request and, in some cases, after authenticating the user, identify the machine learning model 211 via the identifier. The analytics server 210a may transmit the identified machine learning model 211 to the end-user device 240 or send an alert indicating the end-user device is authorized to access the model(s) 211. Upon receipt or access to the machine learning model 211, the end user device 240 may perform the systems and methods described herein to train the machine learning model 211.

The analytics server 210a may store machine learning models 211 (e.g., neural networks, random forest, support vector machines, or other deep learning models) that are trained to predict the anatomical structure represented by various pixels or voxels of a medical image. Various machine learning techniques may involve training the machine learning models to predict (e.g., estimate the likelihood of) each pixel or voxel of a medical image being associated with or otherwise representing a particular anatomical structure, or excluding a particular anatomical structure, based on outputs of AI-based atlas mapping slice localization.

Machine learning models 211 may be stored in the system database 210b and may correspond to individual radiotherapy clinics or otherwise different sets of radiotherapy machines (e.g., radiotherapy machines that are located at individual radiotherapy clinics, are located in different geographical regions, treat specific types of diseases (e.g., different types of cancer), treat specific genders, etc.). For example, the machine learning model 211 may be associated with an identifier indicating the radiotherapy clinic, set of radiotherapy machines, or a specific disease.

In various embodiments, machine learning models 211 use one or more deep learning engines to perform automatic segmentation of image data for radiotherapy treatment planning. Although exemplified using deep convolutional neural networks, it should be understood that any alternative and/or additional deep learning model(s) may be used to implement deep learning engines. The deep learning engines include processing pathways that are trained during training phase. Once trained, deep learning engines may be used (e.g., by a clinician) to perform automatic segmentation for current patients during inference phase.

The aim of the training phase is to train a deep learning engine to perform automatic classification of input segmentation data by mapping the input data (segmentation data) to example output data (labels). The training phase may involve finding weights that minimize the training error between training label data and estimated label data generated by deep learning engine. Disclosed systems and methods apply the 2D anatomical landmarks method to train a deep learning model using data labeled via this method (e.g., ground truth detection). Once the training data is labeled, the deep learning model learns visual attributes of a certain anatomical region and can identify numerical values for the anatomical region that correspond to localized slices within an atlas or reference CT. In practice, by training a contouring model using data labeled via 2D anatomical landmarks method, if a contouring machine learning model knows that an input CT is taken from a particular patient anatomic region, the contouring machine learning model does not need to run analysis that is specific to another anatomic region. In another example, deep learning contouring models may be trained for specific anatomical regions. For example, one model may be specially trained to identify organs in a patient's head and neck.

Figure 3:
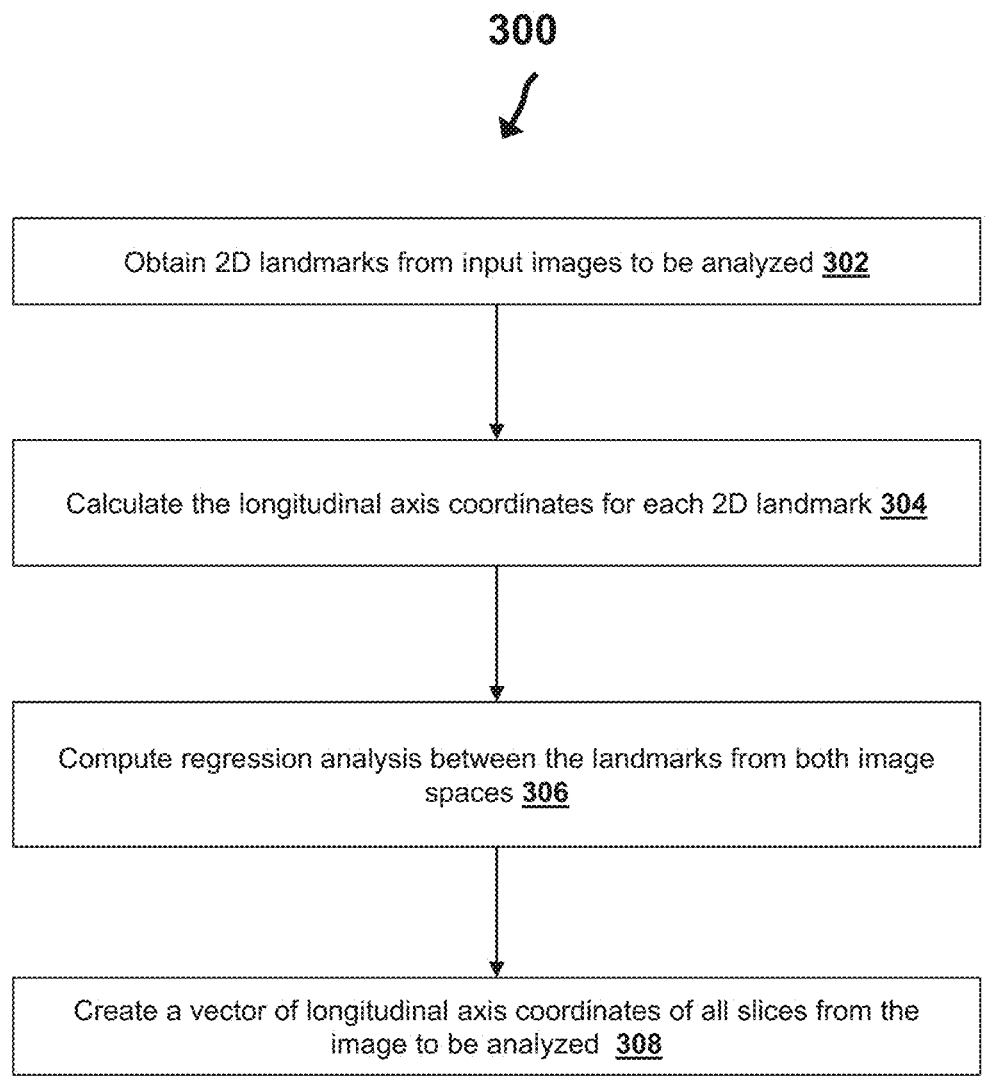
FIG. 3 illustrates a flow diagram of a process for generating training data for AI-based atlas mapping slice localization, according to an embodiment.

FIG. 3 illustrates a flow diagram of a process for generating training data for AI-based atlas mapping slice localization. The method 300 may include steps 302-308. However, other embodiments may include additional or alternative steps, or may omit one or more steps altogether.

The method 300 is described as being executed by an analytics server, such as the analytics server described in FIG. 2. The analytics server may employ one or more processing units, including but not limited to CPUs, GPUs, or TPUs, to perform one or more steps of method 200. The CPUs, GPUs, and/or TPUs may be employed in part by the analytics server and in part by one or more other servers and/or computing devices. The servers and/or computing devices employing the processing units may be local and/or remote (or some combination). For example, one or more virtual machines in a cloud may employ one or more processing units, or a hybrid processing unit implementation, to perform one or more steps of method 300. However, one or more steps of method 300 may be executed by any number of computing devices operating in the distributed computing system described in FIG. 2. For instance, one or more computing devices may locally perform part or all of the steps described in FIG. 3.

In step 302, the analytics server obtains 2D landmarks from the images to be analyzed using a landmark detection algorithm. In various embodiments, this step obtains anatomic landmarks. In an embodiment, the 2D landmarks are 2D slices of the images that match the landmarks defined on a reference image (e.g., atlas).

In step 304, the analytics server calculates the longitudinal axis coordinates (z-axis coordinates) for each 2D landmark. In various embodiments, the longitudinal axis coordinates are z-axis coordinates. In various embodiments, this step calculates the longitudinal axis coordinates on both spaces, a space of the image to be analyzed and a reference image space.

In step 306, the analytics server computes regression analysis between the landmarks from both image spaces. In an embodiment, the regression analysis uses piecewise linear regression techniques. In an embodiment, the regression analysis uses linear regression. In an embodiment, the regression analysis recognizes every 2D slice of the images to be analyzed.

In step 308, the analytics server creates a vector of longitudinal axis coordinates of all slices from the image to be analyzed. In an embodiment of step 308, this vector is mapped to the vector of the reference image using estimated regression coefficients from step 306.

Figure 4:
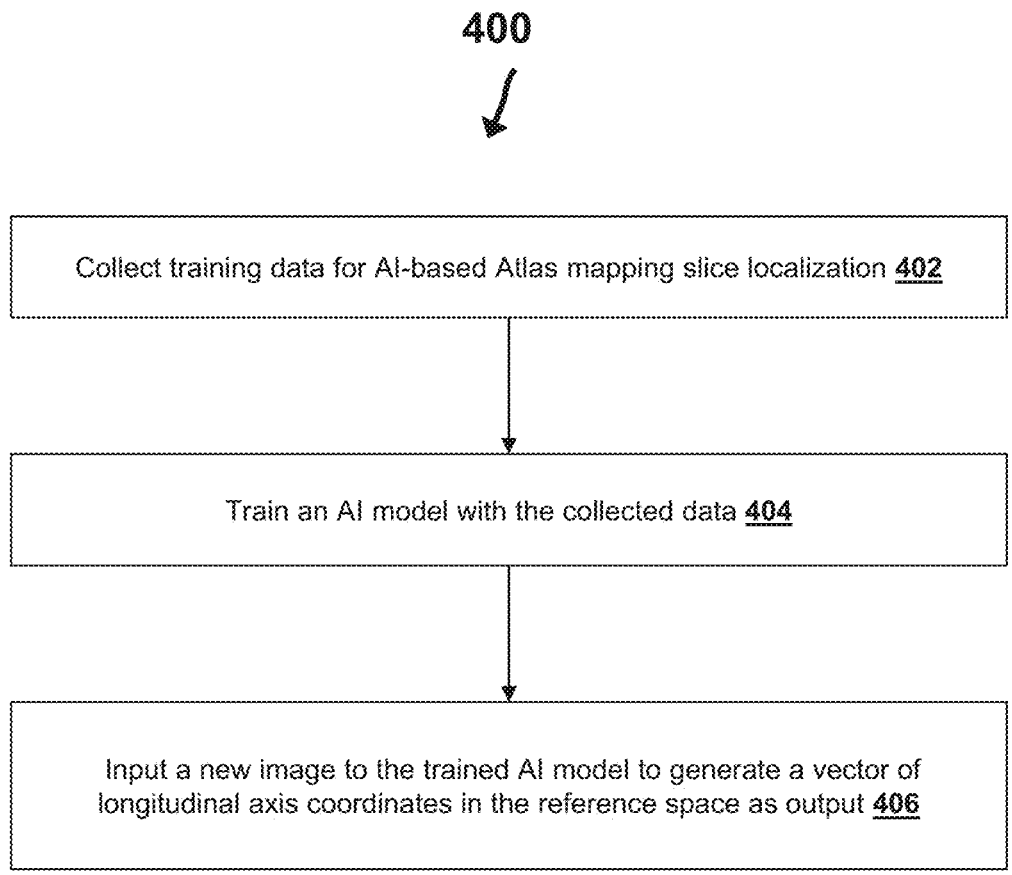
FIG. 4 illustrates a flow diagram of a process using training data for AI-based atlas mapping slice localization to train a deep learning network, according to an embodiment.

FIG. 4 illustrates a flow diagram of a process executed in the analytics server. The method 400 uses training data for AI-based atlas mapping slice localization to train a deep learning network. In an embodiment, the method 400 uses training data generated in the method 300 of FIG. 3.

In step 402, the analytics server collects training data for AI-based atlas Mapping slice localization. In an embodiment, the training data includes images from step 302 and coordinate vectors created in step 308 in the method of FIG. 3.

In step 404, the analytics server train an AI model with the collected training data from step 402. In an embodiment, step 404 trains a 3D neural network to develop an AI-based atlas Mapping Slice Localizer. In an embodiment shown in FIG. 6, the 3D neural network is a convolutional neural network.

In step 406, following model training at step 404, the trained AI-based atlas Mapping Slice Localizer model is applied to a new image. In an example shown in FIG. 7, slices from a new image are provided as input. The model generates a vector of longitudinal axis coordinates in the reference space as output. The coordinates are mapped to the known positions (e.g., anatomical regions) from the reference image. In an embodiment, subsequently the coordinates are mapped to known positions (e.g., anatomical regions) from the reference image.

Figure 5:
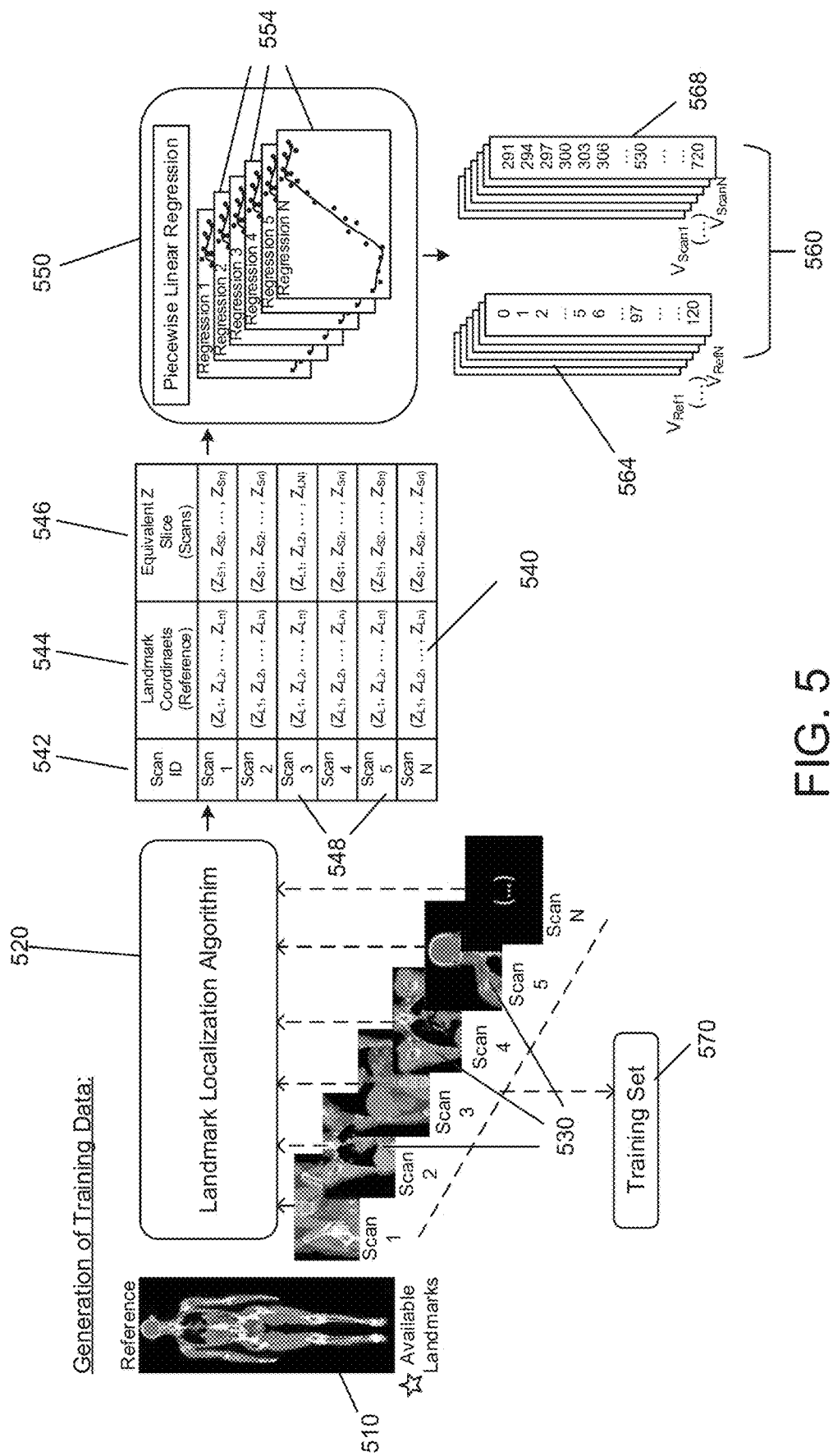
FIG. 5 is a schematic diagram of an image processing based landmark localization procedure, according to an embodiment.

FIG. 5 shows a schematic diagram of an image processing based landmark localization procedure 500. Generated training data may be used to train a deep learning network that maps each slice of an input medical image to a position in a reference system based upon a reference medical image of the human anatomy. The reference system can be a scale along the Z-axis of the human anatomy indicating reference positions for known anatomic landmarks in the reference human anatomy. This mapping maps each slice in the input medical image to a position along the longitudinal body axis in the reference medical image.

A landmark localization algorithm 520 receives as inputs a set of input CTs 530 and a reference CT or atlas 510. The algorithm labels the input images based on the atlas. To generate the ground truth, the algorithm provides a Z-coordinate mapping of an input image to the atlas. The input images 530 may include clinical patient CTs from many different patients. In an embodiment, the input CTs cover all five regions of the axial body: head, neck, thorax (chest and back), abdomen, and pelvis, excluding the extremities. In an embodiment, there is only one atlas image 510.

The landmark localization algorithm 520 identifies a set of localized anatomic regions or points in the body. These localized regions are called landmarks. Landmarks are usually bones, which have a particular shape that can identify a localized region of the body. As to landmarks in an input CT 530, the landmark localization algorithm 520 knows the positions of corresponding landmarks in the reference image or atlas 510. Therefore, when the algorithm 520 detects a landmark in the input CT 530, it knows the coordinates of a corresponding landmark in the atlas 510.

Since anatomic landmarks are known locations that can be detected with some confidence, the selection of anatomic landmarks depend on the region of interest. For example, in the pelvis region, the anatomic landmarks may include crista iliaca superior, os pubis, acetabulum, trochanter major, and symphysis points. In the thorax region the anatomic landmarks may include cervix middle, axilla middle, thorax superior, thorax middle, and trachea bifurcation.

In some embodiments, the anatomic landmarks in a 3D image can be detected by pattern matching. Detection of anatomic landmarks by pattern matching generally involves an optional prefiltering, use of a limited search range within the 3D image, a template (or predefined pattern), and a difference function. Finding the landmark this way means to find the best matching position of the template in the 3D image.

In some embodiments, anatomic landmarks are detected by image plane feature classification. Image plane features are properties of the input image slices. Typical image plane features include the width of the bounding box of all body segments, height of the bounding box of all body segments, sum of areas of all high density segments, number of high density segments, and area of the largest low density segment, etc. In some specific locations of the anatomy, such as the shoulder or the iliac crest, these features or functions of these features have very typical values.

A confidence value can be assigned to each identified landmark. The confidence value can be a value between 0 and 1 and indicates how reliably the landmark has been found.

The process constructs landmarking table 540 after anatomic landmarks are identified. Landmarking table 540 is a table that describes the relation of the image slices being processed to a reference system of the human anatomy. The reference system can be a scale along the Z axis (craniocaudal axis) of the human body, extending from the head to the feet. Reference system Z positions can be stored in millimeters. The landmarking table describes a correspondence relation in one dimension and is stored as a one-dimensional array as follows. Landmarking table 540 includes a row for each input CT scan (slice). The table includes a scan ID 542 for each CT scan, landmark Z coordinates 544 in the reference image, and equivalent Z slice 546 in the CT scan.

The landmarking table 540 is constructed by finding well-defined landmarks, the corresponding positions of which in the reference system are known in the reference CT 510. In mapping an input CT to an anatomical region, mapping needs more than one landmark. In an example of the algorithm 500, most of the time there were three landmarks but sometimes only two. The reference positions for the remaining image slices, where no landmarks were found, are determined by interpolation. A linear interpolation requires at least two points. Given multiple landmarks and interpolation between the landmarks, the algorithm can map a slice in the CT scan to a corresponding slice in the atlas 510. Given the list of landmark positions in the CT image and the list of corresponding reference positions, building the landmarking table can be formulated as a 1-dimensional point based non-rigid registration. Due to variations in landmark positions among human individuals, a transformation between the reference system and actual patient may not be linear.

Landmarks are not always visible or easily identified. In addition, mapping landmarks can introduce significant error. The algorithm 500 may apply filters to recognize and address cases in which the landmarks and/or the interpolation are unclear or inaccurate in building the mapping. In an example, the algorithm employed a 2D anatomical landmarks method, using vector field interpolation to determine reference positions for the image slices in which no landmarks were found. In this example, filtering addressed very small CT images with only one landmark, in which vector field interpolation might fail. Another reason to filter could include anomalous geometry among three landmarks.

A further example of filtering limits mapping of input CT images to atlas within acceptable slope values. If anatomical dimensions in an input CT image are the same size as anatomical dimensions in the atlas, the slope is 1. If anatomical dimensions in the input CT image are larger than in the atlas, the slope is greater than 1, while if anatomical dimensions in the input CT image are smaller than the atlas, the slope is smaller than 1. Filtering can recognize and correct slope values that are much greater than 1 or much smaller than 1.

In addition to mapping CT images to atlas using landmarks, the algorithm 500 for generation of training data includes an additional stage of piecewise linear regression to build the ground truth. Using piecewise linear regression 550, the model will find its own localized features. Piecewise linear regression can find many localized features and build a system that is much more flexible and resilient. Piecewise linear regression employs the principle of modeling the regression function in "pieces," for data that follows different linear trends over different regions of the data. The piecewise linear regression applies the regression analysis to a plurality of regression segments 554 (e.g., Regression1, Regression2, Regression3) corresponding to 2D CT scan slices from the set of input images. Using piecewise linear regression, the regression analysis recognizes each and every CT scan slice.

Mappings 560 map all slices of input images (e.g., respective mappings 564, 568) to the reference atlas image. In an embodiment, each mapping includes a vector of longitudinal axis coordinates of all slices from the respective input image. The vector is mapped to the vector of the reference image using estimated regression coefficients from piecewise linear regression 550.

Training set 570 stores training data from the algorithm 500. In an embodiment, the training data includes images (CT scans) 530 and coordinate vectors 560.

Figure 6:
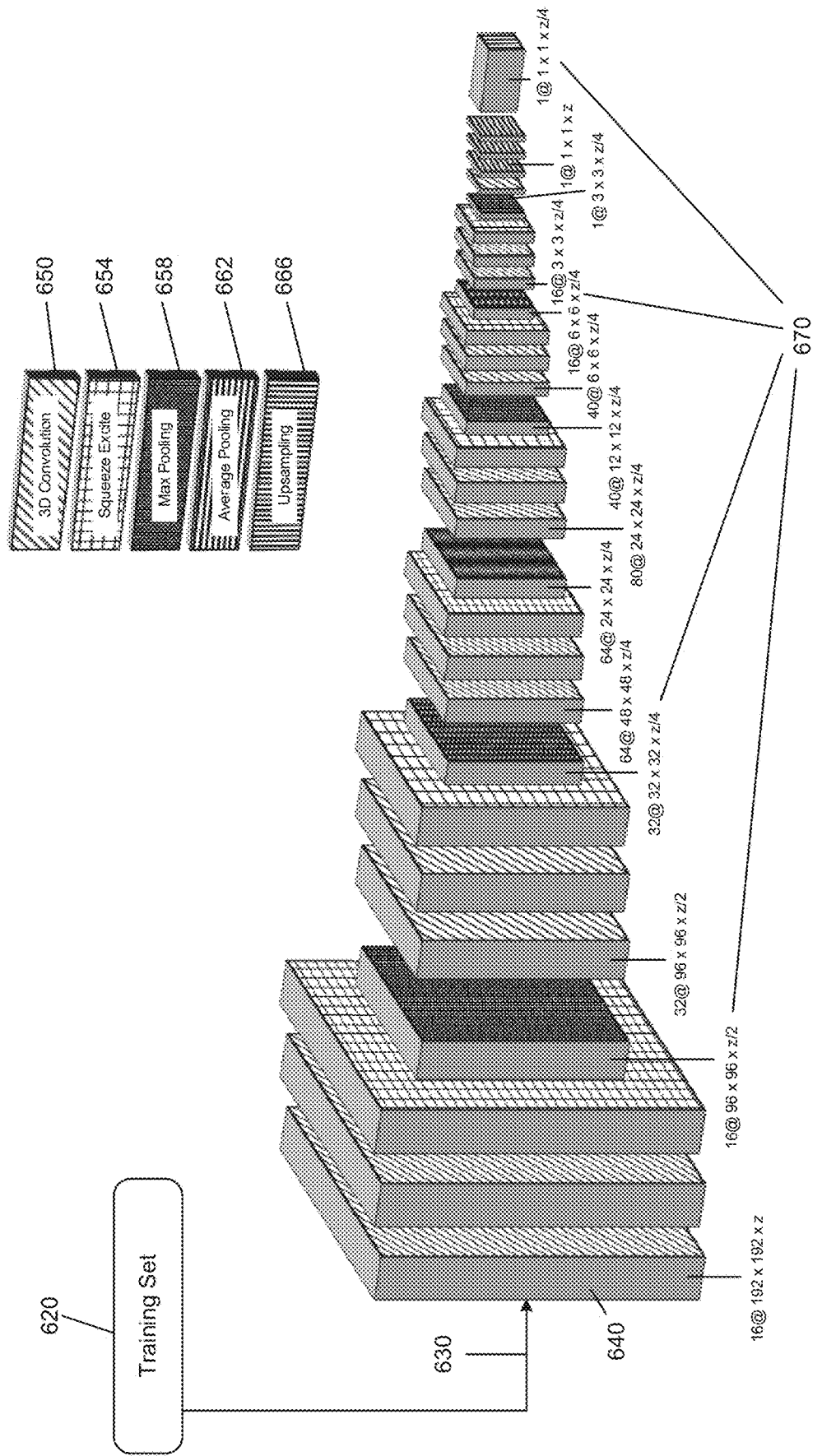
FIG. 6 illustrates an architecture of a deep learning network for training an AI-based atlas mapping slice localizer model, according to an embodiment.

FIG. 6 illustrates an architecture of a deep learning network 600 for developing an AI-based atlas mapping slice localizer. Training set 620 collects training data for AI-based atlas mapping slice localization, e.g., received from training set 570, as inputs 630 to the deep learning network. In an embodiment, the training data includes input images (CT scans) 530 and coordinate vectors collected at 570 in the algorithm of FIG. 5.

In the illustrated embodiment, deep learning network 600 is a convolutional neural network (CNN). A CNN is a branch of neural networks and consists of a stack of layers each performing a specific operation, e.g., convolution, pooling, loss calculation, etc. Each intermediate layer receives the output of the previous layer as its input. The beginning layer is an input layer, which is directly connected to an input image. The next set of layers are convolutional layers that present the results of convolving a certain number of filters with the input data and perform as a feature extractor. The output of each convolution layer is considered as an activation map, which highlights the effect of applying a specific filter on the input. Convolutional layers may be followed by activation layers to apply non-linearity to the activation maps. The next layer can be a pooling layer that helps to reduce the dimensionality of the convolution's output. In various implementations, high-level abstractions are extracted by fully connected layers. The weights of neural connections and the kernels may be continuously optimized in the training phase. A computer can be provided with a large dataset and, by using deep learning algorithms, can sort elements of the data into categories such as function, shape, etc.

In the example architecture of FIG. 6, a deep learning network is designed as a six-stage 3D CNN 640. CNN 640 includes a 3D convolution layer 650 followed by squeeze-and-excitation layer 654 and max-pooling layer 658. These layers are followed by another 3D convolution layer, three average pooling layers 662, and a final up-sampling layer 666 that acts as the output layer of CNN 640. Neurons in the layers of CNN 640 are arranged in three dimensions (width, height, and depth) 670. In an embodiment, the CNN input 630 is a three-dimensional image (CT volume) with dimensions $N_x$, $N_y$, $N_z$, and the output is a one dimensional vector with dimension $N_z$ containing the reference image mapped coordinates of each input image slice.

Figure 7:
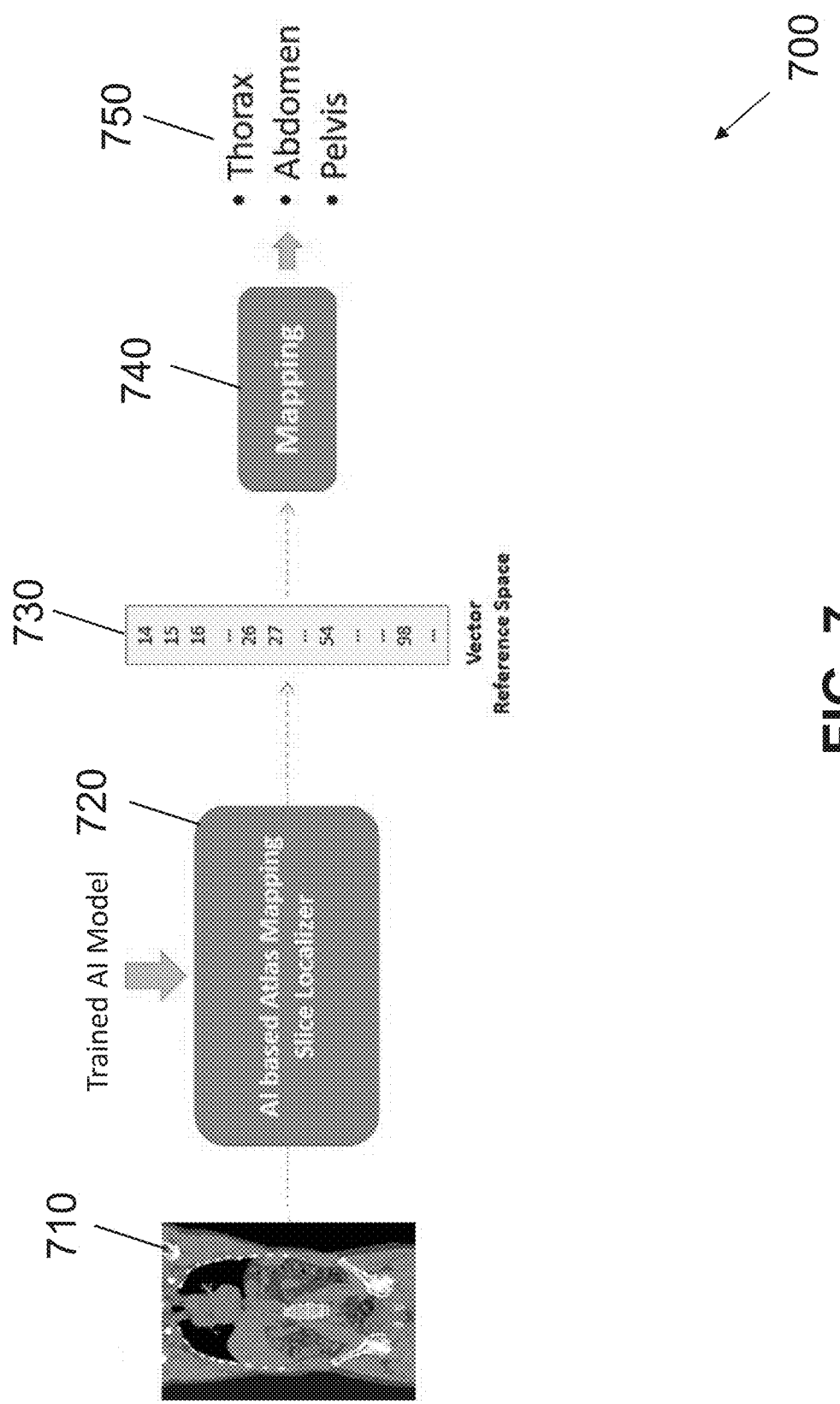
FIG. 7 illustrates a process for applying a trained AI-based atlas mapping slice localizer model to an input image to generate a vector of longitudinal axis coordinates, and for mapping the coordinates to known positions from the atlas image, according to an embodiment.

As illustrated in the flow diagram 700 of FIG. 7, once the AI-based atlas mapping slice localizer has been trained it may be applied to new input images for mapping slice localization. Images slices from a new image (CT scan) 710 are provided as input. The AI-based atlas mapping slice localizer model 720 outputs a vector 730 of z-axis coordinates in the reference space. Subsequently, the coordinates are mapped 740 to known positions from the reference image, e.g., anatomical regions 750. In automatic segmentation of a clinical patient medical image such as a CT scan, these mapping outputs 730, 750 can be used to select suitable computer model(s) from a library of computer models for contouring the patient image. These mapping outputs can be applied by a scheduler in selecting and prioritizing tasks in computer automated organ detection/segmentation (CAD) systems.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What we claim is:

1. A method comprising:
   executing, by a processor, a machine learning model that receives an input of a first image of an anatomical region of a patient depicting a first organ having an outline to cause the machine learning model to predict boundary information of the anatomical region within a reference image;
   selecting, by the processor, a computer model from a library of computer models based on the boundary information of the anatomical region, the computer model configured to execute a contouring protocol identifying outlines of organs within anatomical regions; and
   transmitting, by the processor, the boundary information of the anatomical region of the first image to the computer model based on selecting the computer model from the library of computer models, whereby the computer model executes the contouring protocol to identify the outline of the first organ within the anatomical region.

2. The method of claim 1, wherein the computer model is a second machine learning model configured to ingest the first image and identify the contour within the anatomical region.

3. The method of claim 1, wherein the machine learning model outputs a mapping of a slice from the first image to the reference image.

4. The method of claim 1, wherein the machine learning model is trained based on a set of second images of a set of second anatomical regions depicting a set of second organs having a set of second outlines.

5. The method of claim 4, wherein at least one second image within the set of second images is labeled based on a reference point within the at least one second image to a corresponding anatomical region within the reference image.

6. The method of claim 1, wherein the boundary information comprises a first limit and a second limit.

7. A method, comprising:
   receiving, by a processor, a set of medical images comprising at least a first image and an atlas image, each image containing a plurality of two dimensional (2D) anatomic landmarks;
   calculating, by the processor, longitudinal axis coordinates for each of the plurality of 2D anatomic landmarks in a first image space of the first image of the set of medical images and for each of the corresponding landmarks of the plurality of 2D anatomic landmarks in a reference image space of the atlas image;
   executing, by the processor, a regression analysis between each of the 2D anatomic landmarks of the first image space and the corresponding 2D landmarks of the reference image space, wherein the regression analysis is applied to a plurality of regression segments corresponding to 2D slices from the set of medical images;

generating, by the processor, a vector of longitudinal axis coordinates for each slice of the medical images of the set of medical images;

mapping, by the processor, each vector of longitudinal axis coordinates of the first image to the atlas image; and providing, by the processor, data associated with each vector of longitudinal axis coordinates to an analytics server to train a localizer model.

8. The method of claim 7, wherein each of the 2D anatomic landmarks is one of the 2D slices from the first image that matches the corresponding 2D landmark defined on the atlas image.

9. The method of claim 7, wherein the atlas image is a full body atlas, and wherein the longitudinal axis coordinates in the reference image space of the atlas image are coordinates within a total cranial-caudal range along a longitudinal body axis in the full body atlas.

10. The method of claim 7, wherein the regression analysis between the 2D anatomic landmarks and the corresponding 2D landmarks is a piecewise linear regression.

11. The method of claim 10, wherein the piecewise linear regression applies the regression analysis to the plurality of regression segments corresponding to the 2D slices from the set of medical images.

12. The method of claim 7, wherein the vector of longitudinal axis coordinates for each of the medical images encompasses all 2D slices from the first image.

13. The method of claim 7, wherein the vector of longitudinal axis coordinates for each of the medical images is mapped to the atlas image via estimated regression coefficients.

14. The method of claim 7, further comprising training, by the processor, a deep learning model to determine a vector of longitudinal axis coordinates in an image space of an image analyzed by the model, wherein the deep learning model receives the set of medical images and the vector of longitudinal axis coordinates for each of the medical images as training inputs.

15. A system comprising:
a server comprising a processor and a non-transitory computer-readable medium containing instructions that when executed by the processor causes the processor to perform operations comprising:
execute a machine learning model that receives an input of a first image of an anatomical region of a patient depicting a first organ having an outline to cause the machine learning model to predict boundary information of the anatomical region within a reference image;
select a computer model from the library of computer models to execute a contouring protocol, whereby the contouring protocol identifies the outline of the first organ within the anatomical region; and
transmit the boundary information of the anatomical region of the first image to the computer model based on selecting the computer model form the library of computer models, whereby the computer model executes the contouring protocol to identify the outline of the first organ within the anatomical region.

16. The system of claim 15, wherein the machine learning model is trained based on a set of second images of a set of second anatomical regions depicting a set of second organs having a set of second outlines.

17. The system of claim 16, wherein at least one second image within the set of second images is labeled based on a reference point within the at least one second image to a corresponding anatomical region within the reference image.

18. The system of claim 15, wherein the boundary information comprises a first limit and a second limit.

* * * * *